(12) United States Patent
Kew

(10) Patent No.: US 6,415,795 B1
(45) Date of Patent: Jul. 9, 2002

(54) PROTECTIVE FOOT COVERING

(76) Inventor: Jonathan L. Kew, 49 Marlborough Rd, Maidenhead Berkshire SL6-4LF (GB)

(*) Notice: Subject to any disclaimer, the term of this patent is extended or adjusted under 35 U.S.C. 154(b) by 0 days.

(21) Appl. No.: 09/727,418

(22) Filed: Dec. 1, 2000

(51) Int. Cl.[7] .............................................. A61B 19/00
(52) U.S. Cl. ........................ 128/869; 128/882; 602/60; 602/61; 602/63
(58) Field of Search ................................ 602/5, 12, 23, 602/24, 27–29, 60–62, 63, 65, 66; 128/882, 869

(56) References Cited

U.S. PATENT DOCUMENTS

| 2,515,903 A | * | 7/1950 | Sjoquist | |
|---|---|---|---|---|
| 4,603,698 A | * | 8/1986 | Cherniak | 36/162 |
| 5,007,416 A | * | 4/1991 | Burns et al. | 602/27 |
| D325,088 S | * | 3/1992 | O'Brien et al. | |
| 5,372,575 A | * | 12/1994 | Sebastian | 602/20 |
| 5,545,129 A | * | 8/1996 | Snook | |
| 5,607,756 A | * | 3/1997 | Yamauchi et al. | |
| 5,795,316 A | * | 8/1998 | Gaylord | 602/27 |
| 5,840,053 A | * | 11/1998 | Roth | |
| 5,897,518 A | * | 4/1999 | Shaw | |
| 6,234,988 B1 | * | 5/2001 | Brother et al. | 602/65 |

* cited by examiner

Primary Examiner—Denise M. Pothier
Assistant Examiner—Lalita M Hamilton

(57) ABSTRACT

A protective foot covering for preventing blisters and sores while running or walking. The protective foot covering includes a sleeve being adapted to fit about a foot of a user; and also includes an insert retaining member being securely disposed in the sleeve; and further includes a first padded insert member being securely and removably retained in the sleeve; and also includes a second padded insert member being securely and removably retained in the sleeve.

9 Claims, 2 Drawing Sheets

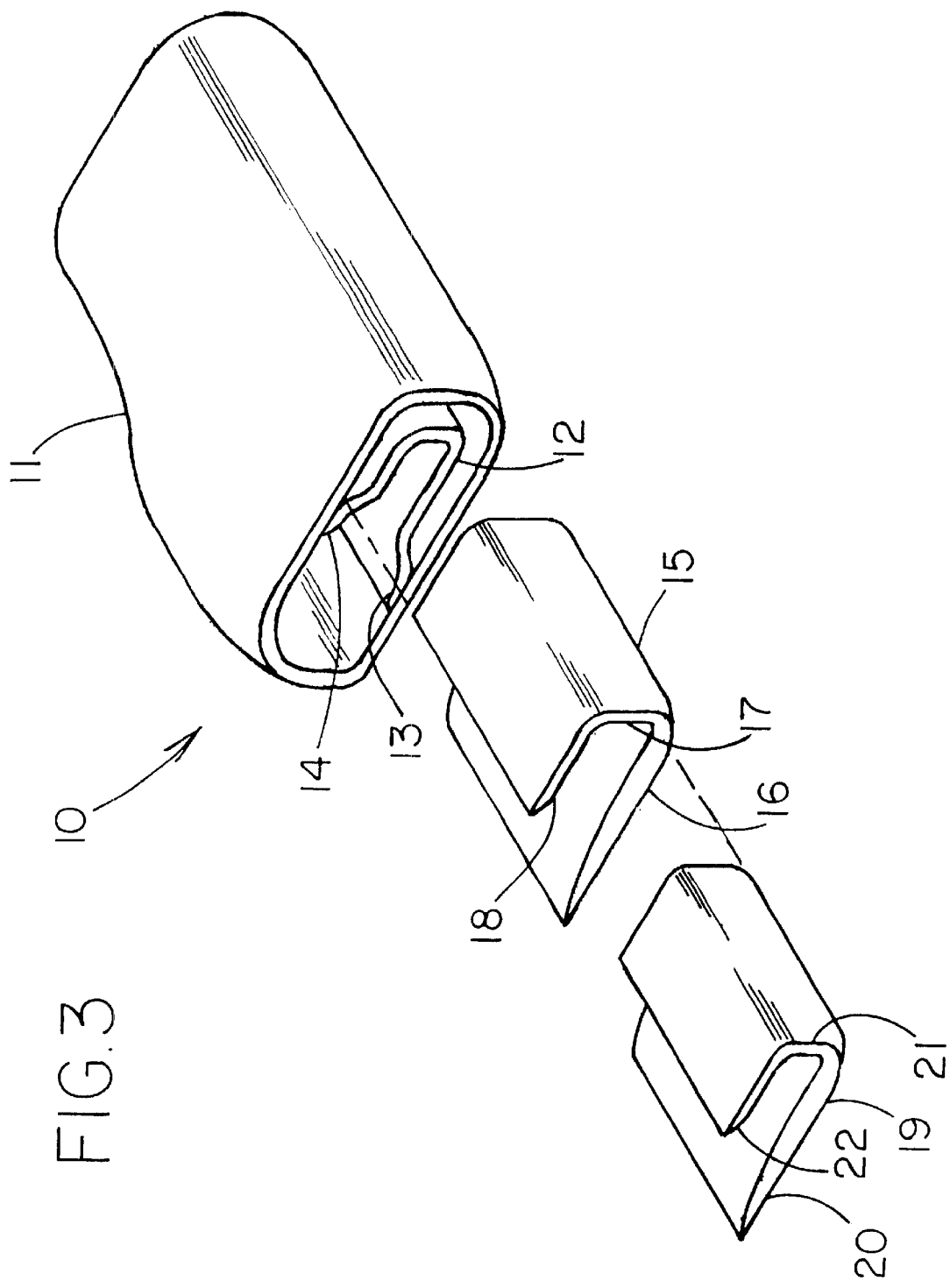

PROTECTIVE FOOT COVERING

BACKGROUND OF THE INVENTION

1. Field of the Invention

The present invention relates to a foot cushion and more particularly pertains to a new protective foot covering for preventing blisters and sores while running or walking.

2. Description of the Prior Art

The use of a foot cushion is known in the prior art. More specifically, a foot cushion heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 5,607,756; 5,840,053; 5,545,129; 5,897,518; 2,515,903; and U.S. Pat. No. Des. 325,088.

While these devices fulfill their respective, particular objectives and requirements, the aforementioned patents do not disclose a new protective foot covering. The inventive device includes a sleeve being adapted to fit about a foot of a user; and also includes an insert retaining member being securely disposed in the sleeve; and further includes a first padded insert member being securely and removably retained in the sleeve; and also includes a second padded insert member being securely and removably retained in the sleeve.

In these respects, the protective foot covering according to the present invention substantially departs from the conventional concepts and designs of the prior art, and in so doing provides an apparatus primarily developed for the purpose of preventing blisters and sores while running or walking.

SUMMARY OF THE INVENTION

In view of the foregoing disadvantages inherent in the known types of foot cushion now present in the prior art, the present invention provides a new protective foot covering construction wherein the same can be utilized for preventing blisters and sores while running or walking.

The general purpose of the present invention, which will be described subsequently in greater detail, is to provide a new protective foot covering which has many of the advantages of the foot cushion mentioned heretofore and many novel features that result in a new protective foot covering which is not anticipated, rendered obvious, suggested, or even implied by any of the prior art foot cushion, either alone or in any combination thereof.

To attain this, the present invention generally comprises a sleeve being adapted to fit about a foot of a user; and also includes an insert retaining member being securely disposed in the sleeve; and further includes a first padded insert member being securely and removably retained in the sleeve; and also includes a second padded insert member being securely and removably retained in the sleeve.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new protective foot covering which has many of the advantages of the foot cushion mentioned heretofore and many novel features that result in a new protective foot covering which is not anticipated, rendered obvious, suggested, or even implied by any of the prior art foot cushion, either alone or in any combination thereof.

It is another object of the present invention to provide a new protective foot covering which may be easily and efficiently manufactured and marketed.

It is a further object of the present invention to provide a new protective foot covering which is of a durable and reliable construction.

An even further object of the present invention is to provide a new protective foot covering which is susceptible of a low cost of manufacture with regard to both materials and labor, and which accordingly is then susceptible of low prices of sale to the consuming public, thereby making such protective foot covering economically available to the buying public.

Still yet another object of the present invention is to provide a new protective foot covering which provides in the apparatuses and methods of the prior art some of the advantages thereof, while simultaneously overcoming some of the disadvantages normally associated therewith.

Still another object of the present invention is to provide a new protective foot covering for preventing blisters and sores while running or walking.

Yet another object of the present invention is to provide a new protective foot covering which includes a sleeve being adapted to fit about a foot of a user; and also includes an insert retaining member being securely disposed in the sleeve; and further includes a first padded insert member being securely and removably retained in the sleeve; and also includes a second padded insert member being securely and removably retained in the sleeve.

Still yet another object of the present invention is to provide a new protective foot covering that adds comfort to a user's foot.

Even still another object of the present invention is to provide a new protective foot covering that reduces the pain to one's foot.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an exploded perspective view of the present invention.

DESCRIPTION OF THE PREFERRED EMBODIMENT

Figure 1:
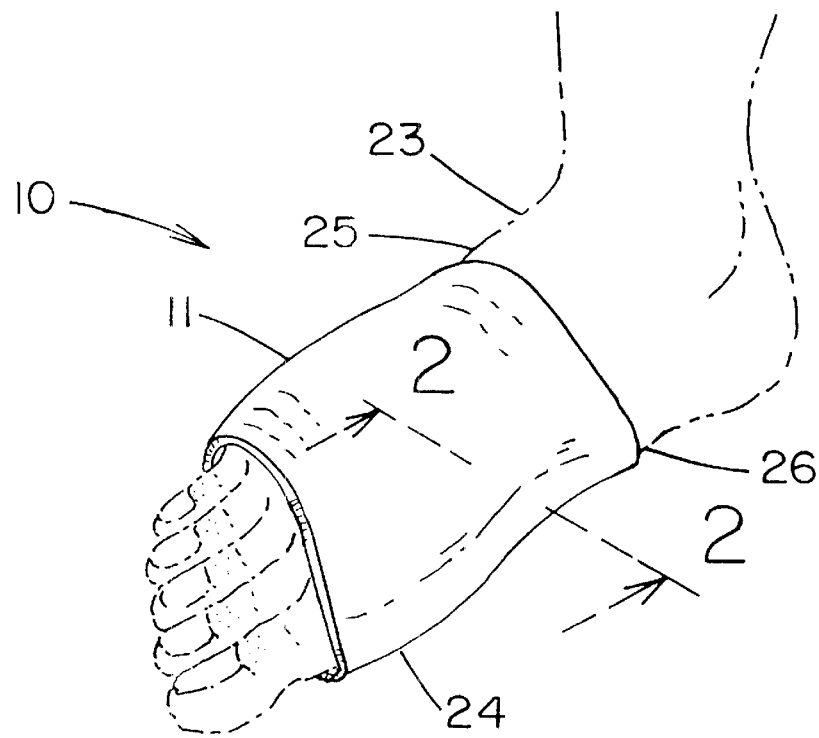
FIG. 1 is a perspective view of a new protective foot covering according to the present invention.
Figure 2:
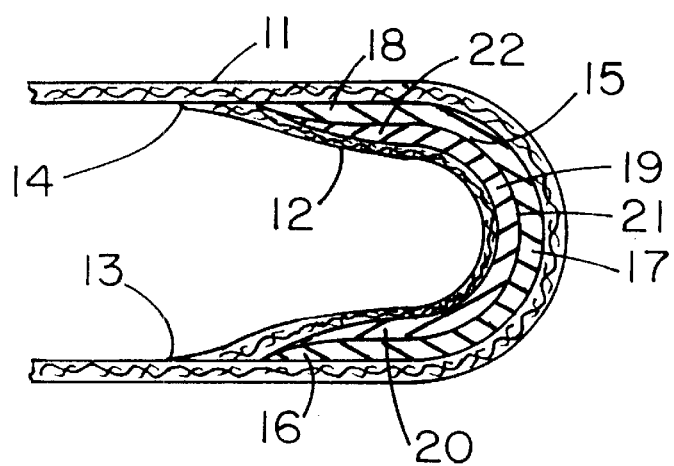
FIG. 2 is a cross-sectional view of the present invention.

With reference now to the drawings, and in particular to FIGS. 1 through 3 thereof, a new protective foot covering embodying the principles and concepts of the present invention and generally designated by the reference numeral 10 will be described.

As best illustrated in FIGS. 1 through 3, the protective foot covering 10 generally comprises a sleeve 11 being adapted to fit about a foot 23 of a user. The sleeve 11 is adapted to snugly fit about a ball 24 and instep 25 of the foot 23 of the user. An insert retaining member 12 is securely and conventionally disposed and sewn in the sleeve 11. The insert retaining member 12 includes longitudinal side edges 13, 14 which are securely sewn and opposedly attached to an interior of the sleeve 11 thus forming a pocket in the sleeve 11.

A first padded insert member 15 is securely and removably retained in the sleeve 11. The first padded insert member 15 is generally a thin piece of material having a first end portion 16, an intermediate portion 17 which is angled relative to the first end portion 16, and a second end portion 18 which is angled relative to the intermediate portion 17 and which is disposed generally parallel to the first end portion 16. The first padded insert member 15 is removably disposed against the interior of the sleeve 11 and between the insert retaining member 12 and the sleeve 11. The first padded insert member 15 is adapted cover an arch 26 of the user's foot 23 and to extend from a top 24 of the user's foot 23 to a bottom of the user's foot 23.

A second padded insert member 19 is securely and removably retained in the sleeve 11. The second padded insert member 19 is generally a thin piece of material having a first end portion 20, an intermediate portion 21 which is angled relative to the first end portion 20, and a second end portion 22 which is angled relative to the intermediate portion 21 and which is disposed generally parallel to the first end portion 20. The second padded insert member 19 is removably disposed against the insert retaining member 12 between the insert retaining member 12 and the first padded insert member 15. The first and second padded insert members 15, 19 are made of rubberized material.

In use, the extends the protective foot covering 10 about one's foot 23 and can slip a sock and shoe over the protective foot covering 10 and can either run or walk with the protective foot covering 10.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A protective foot covering comprising:

a sleeve for receiving a foot of a user;

an insert retaining member disposed in said sleeve;

a first padded insert member removably retained in said sleeve; and a second padded insert member removably retained in said sleeve;

wherein said first padded insert member is generally a thin piece of material having a first end portion, an intermediate portion which is angled relative to said first end portion, and a second end portion which is angled relative to said intermediate portion and which is disposed generally parallel to said first end portion, said first padded insert member being removably disposed against said interior of said sleeve and between said insert retaining member and said sleeve, and first padded insert member being adapted to cover an arch of the user's foot and to extend from a top of the user's foot to a bottom of the user's foot.

2. A protective foot covering as described in claim 1, wherein said sleeve is adapted to snugly fit about a ball and instep of the foot of the user.

3. A protective foot covering as described in claim 1, wherein said insert retaining member includes longitudinal side edges which are attached to an interior of said sleeve thus forming a pocket in said sleeve.

4. A protective foot covering as described in claim 1, wherein said second padded insert member is generally a thin piece of material having a first end portion, an intermediate portion which is angled relative to said first end portion, and a second end portion which is angled relative to said intermediate portion and which is disposed generally parallel to said first end portion, said second padded insert member being removably disposed against said insert retaining member between said insert retaining member and said first padded insert member.

5. A protective foot covering as described in claim 4, wherein said first and second padded insert members are made of rubberized material.

6. A protective foot covering comprising:

a sleeve being adapted to fit about a foot of a use;

insert retaining member being securely disposed in said sleeve;

a first padded insert member being securely and removably retained in said sleeve; and a second padded insert member being securely and removably retained in said sleeve.

wherein said insert retaining member includes longitudinal side edges which are securely and opposedly attached to an interior of said sleeve thus forming a pocket in said sleeve;

wherein said first padded insert member is generally a thin piece of material having a first end portion, an intermediate portion which is angled relative to said first end portion, and a second end portion which is angled relative to said intermediate portion and which is disposed generally parallel to said first end portion, said first padded insert member being removably disposed against said interior of said sleeve and between said insert retaining member and said sleeve, said first padded insert member being adapted to cover an arch of the user's foot and to extend from a top of the user's foot to a bottom of the user's foot.

7. A protective foot covering as described in claim 6, wherein said second padded insert member is generally a thin piece of material having a first end portion, an intermediate portion which is angled relative to said first end portion, and a second end portion which is angled relative to said intermediate portion and which is disposed generally parallel to said first end portion, said second padded insert member being removably disposed against said insert retaining member between said insert retaining member and said first padded insert member.

8. A protective foot covering as described in claim 7, wherein said first and second padded insert members are made of rubberized material.

9. A protective foot covering comprising:

a sleeve being adapted to fit about a foot of a user, said sleeve being adapted to snugly fit about a ball and instep of the foot of the user;

an insert retaining member being securely disposed in said sleeve, said insert retaining member including longitudinal side edges which are securely and opposedly attached to an interior of said sleeve thus forming a pocket in said sleeve;

a first padded insert member being securely and removably retained in said sleeve, said first padded insert member being generally a thin piece of material having a first end portion, an intermediate portion which is angled relative to said first end portion, and a second end portion which is angled relative to said intermediate portion and which is disposed generally parallel to said first end portion, said first padded insert member being removably disposed against said interior of said sleeve and between said insert retaining member and said sleeve, said first padded insert member being adapted cover an arch of the user's foot and to extend from a top of the user's foot to a bottom of the user's foot; and a second padded insert member being securely and removably retained in said sleeve, said second padded insert member being generally a thin piece of material having a first end portion, an intermediate portion which is angled relative to said first end portion, and a second end portion which is angled relative to said intermediate portion and which is disposed generally parallel to said first end portion, said second padded insert member being removably disposed against said insert retaining member between said insert retaining member and said first padded insert member, said first and second padded insert members being made of rubberized material.

* * * * *